United States Patent [19]
Brenton et al.

[11] Patent Number: 5,469,624
[45] Date of Patent: * Nov. 28, 1995

[54] INTERCHANGEABLE THUMB RINGLETS FOR PIVOTED CUTTING AND GRASPING INSTRUMENTS

[76] Inventors: Billy H. Brenton, 245-B El Cerro Loop, Los Lunas, N.M. 87031; James J. Stagnone, 2426 Vista Grande, NW., Albuquerque, N.M. 87120

[ * ] Notice: The portion of the term of this patent subsequent to Jun. 30, 2009, has been disclaimed.

[21] Appl. No.: 155,007

[22] Filed: Nov. 19, 1993

Related U.S. Application Data

[63] Continuation-in-part of Ser. No. 907,107, Jun. 30, 1992, Pat. No. 5,301,430.

[51] Int. Cl.$^6$ .................................................. B26B 13/00
[52] U.S. Cl. .................................. 30/232; 30/256; 30/260
[58] Field of Search ............................... 30/232, 241, 254, 30/256, 260, 341

[56] References Cited

U.S. PATENT DOCUMENTS

| 187,713 | 2/1877 | Kelly | 30/256 |
| 440,436 | 11/1890 | Pearsall | 30/341 |
| 4,184,249 | 1/1980 | Megna et al. | 30/341 |
| 4,254,551 | 3/1981 | Megna et al. | 30/341 |
| 4,642,895 | 2/1987 | Gauvry | 30/341 |
| 5,125,159 | 6/1992 | Brenton et al. | 30/232 |
| 5,301,430 | 4/1994 | Brenton et al. | 30/232 |

FOREIGN PATENT DOCUMENTS

| 8801248 | 5/1988 | Germany | 30/232 |
| 3928859 | 3/1991 | Germany | 30/341 |

*Primary Examiner*—Hwei Siu Payer
*Attorney, Agent, or Firm*—Samuel M. Freund

[57] ABSTRACT

Interchangeable thumb ringlets are described for improving the comfort and control of scissors and pivoted grasping instruments. Flexible thumb ringlets having various sizes are removably attachable to the thumb handle portion of such instruments, thereby providing proper fit to the user's thumb.

6 Claims, 3 Drawing Sheets

INTERCHANGEABLE THUMB RINGLETS FOR PIVOTED CUTTING AND GRASPING INSTRUMENTS

This is a continuation-in-part of application Ser. No. 07,907,107filed on Jun. 30,1992, now U.S. Pat. No. 5,301,430.

BACKGROUND OF THE INVENTION

The present invention relates generally to pivoted cutting and grasping instruments, and more particularly to the use of interchangeable thumb and index finger ringlets to increase the ease and flexibility of use thereof and to reduce the effort involved and fatigue resulting from prolonged use.

Modifications which would allow for greater comfort for the surgeon or barber in the use of surgical scissors and forceps and hair cutting scissors, respectively, have been few, the most notable being the use of finger and thumb ringlets. However, the advantages deriving from the use of such ringlets, such as better control and reduced fatigue, are significantly decreased if they do not properly fit the user's fingers.

Additionally, numerous beauticians, barbers clothiers, and diverse other professionals who spend long hours using scissors cutting hair, cloth, tissue, and other material suffer from or have an occupational predisposition towards the development of Carpal Tunnel Syndrome, tenosynovitis, and other joint and spine problems. Carpal Tunnel Syndrome involves that portion of the wrist found under the skin which might be in contact with a watchband. The tunnel is defined or formed by collagenous tissue bands which surround the underlying tendons, nerves and bones. In Carpal Tunnel Syndrome, factors which lead to overcrowding within the tunnel and cause compression of the median nerve. The trauma of overuse of the wrist, tendonitis, infection, edema, fractures, tumors, obesity, systemic diseases, and spontaneous cases with no apparent causes might increase the pressure within the tunnel. The increased pressure on the median nerve can result in nerve damage or neuropathy causing a paralysis, sensations of numbness, tingling, and various types of pain. An accompanying tendonitis might cause pain on motion and tenderness to the touch.

Accordingly it is an object of the present invention to provide pivoted cutting and grasping instruments having interchangeable thumb ringlets having various sizes such that virtually any user may comfortably and precisely utilize instruments fitted with them while simultaneously minimizing unnecessary wrist, elbow, and shoulder motion.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the pivoted cutting and grasping devices of this invention include a conventional pivoted cutting or grasping instrument modified to have interchangeable, rotatable and pivotable thumb and finger ringlets or bows attached to the handles thereof.

Preferably, the ringlets are fabricated from soft, but sturdy plastic material to provide additional flexibility in the motion obtainable.

It is preferred that single-piece, hand-adjustable tensioning means be utilized to provide the pivot/tension function more commonly provided by a screw or rivet in conventional pivoted cutting and grasping instruments.

Benefits and advantages of the subject invention include reduction of fatigue and more precise control in the use of the pivoted grasping and cutting devices hereof.

BRIEF DESCRIPTION OF THE DRAWINGS

The accompanying drawings, which are incorporated in and form a part of the specification, illustrate several embodiments of the present invention and, together with the description, serve to explain the principles of the invention. In the drawings.

DETAILED DESCRIPTION OF THE INVENTION

Briefly, the present invention includes the use of interchangeable thumb ringlets for improving the comfort and control of scissors and pivoted grasping instruments. Flexible ringlets having various sizes are removably attached to the handle portions of such instruments, thereby providing proper fit to the user's fingers.

Figure 1A:
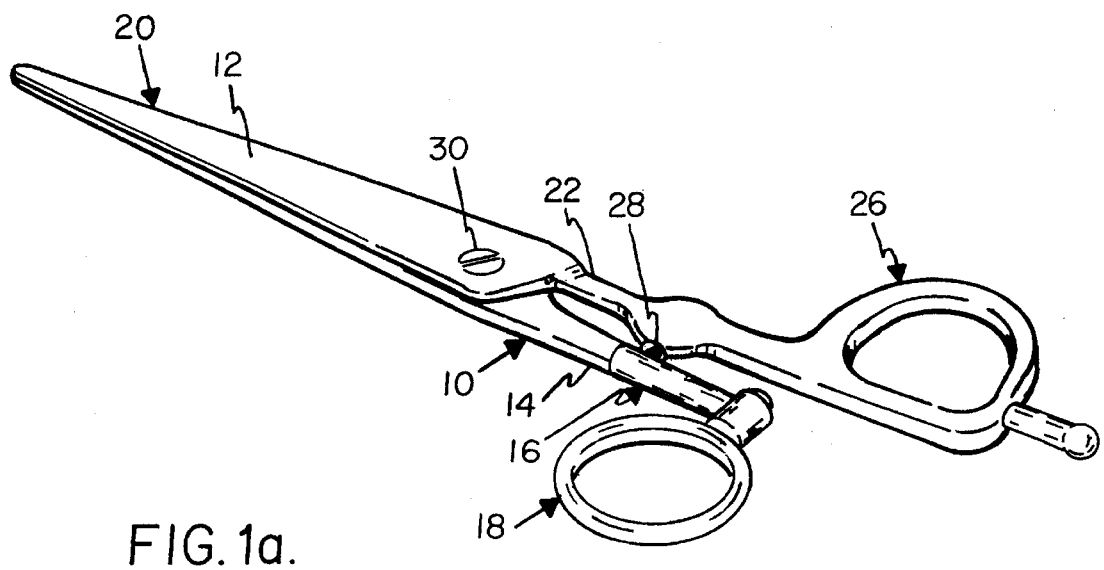
FIG. 1a is a schematic representation of a perspective view of the scissors embodiment of the present invention shown in its closed configuration.

Reference will now be made in detail to the present preferred embodiments of the invention, examples of which are illustrated in the accompanying drawings. Similar or identical structure is identified by identical callouts. In what follows, description will be focused on scissors. However, with minor changes this description is applicable to pivoted grasping instruments as well. Turning now to the figures, FIG. 1a is a schematic representation of a perspective view of the scissors of our invention in its closed configuration. Shank member 20 includes a cutting portion 12 and a handle portion 14. Adjacent shank member 10 is similarly constructed, and has a cutting portion (not shown) and a handle portion 22, shank members 10 and 20 forming a scissors.

Handle extension means 16 is rigidly attached to handle portion 22 and provides a manner in which currently-available scissors may be retrofitted to include interchangeable thumb ringlets. Ringlet 18 is rotatable attached to extension means 16. It is preferred that ringlets be constructed from flexible materials so that additional motion is available to an inserted thumb of the user of the device. Handle portion 14 is shown to be fitted with a standard fixed finger ringlet 26, one of many variations thereof known in the scissors art, and is shown to be longer than opposing handle portion 22 in order to more ergonometrically fit the user's hand. It should be mentioned that handle extension means 16 may be fashioned integrally with shank member 10 in, say, a forging process in order to save fabrication costs. Bumper 28 absorbs a portion of the force which would otherwise be transmitted to the user's hand when the scissors is closed. screw 30 provides the pivot for shank members 10 and 20.

Figure 1B:
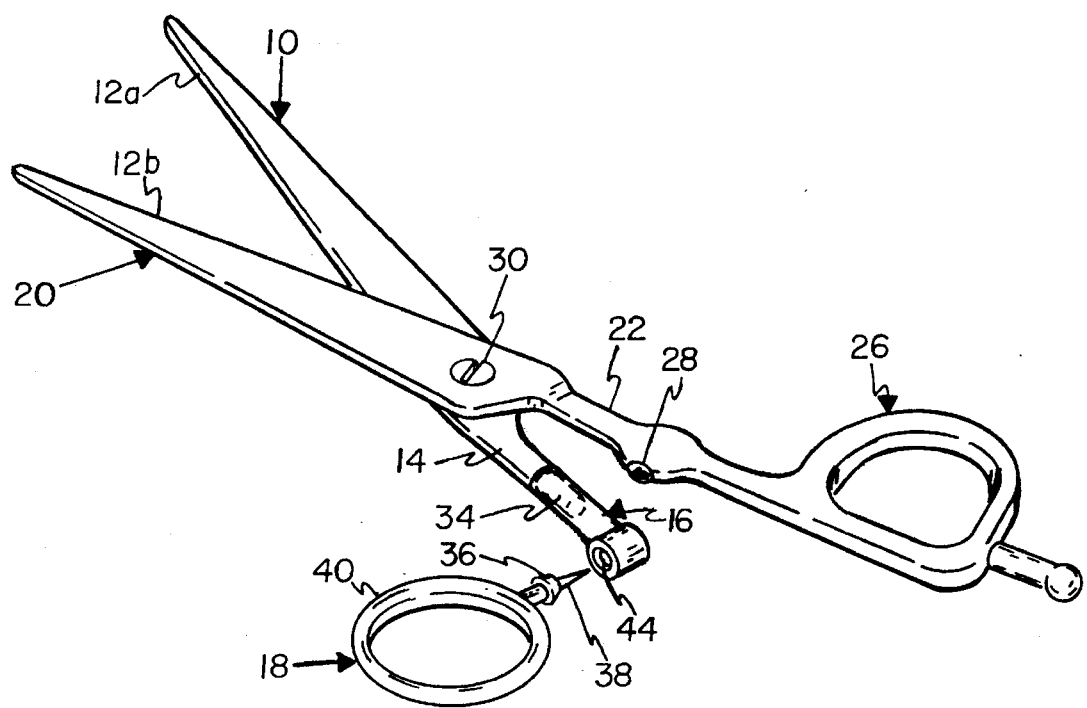
FIG. 1b is a schematic representation of an exploded view of the embodiment of the present invention shown in FIG. 1a showing, in particular, the scissor blades, handles, thumb ringlet, and a bumper.

FIG. 1b is an exploded schematic representation of the scissors shown in FIG. 1a hereof, more clearly showing the component parts thereof. Shown also are modifications to the thumb handle portion of a commercial scissors 32 in which the conventional thumb ringlet thereof has been removed in order to adapt it for attachment of handle extension means 16. respectively. Of course, as stated above, one could have originally fabricated scissors having a handle adapted to receive ringlets 18 directly and without the need for extensions. Ringlet 18 is fabricated having an arm 36 disposed generally radially to a ring member 40 adapted to be rotatably inserted into holes 14 in handle extension 16 said arm having a deformable enlarged portion at the terminus thereof. Extension arm 38 are sturdily attached to the enlarged portions of arm 36 and is adapted to be readily inserted into hole 44 in order to permit the deformable enlarged portion to be pulled through the holes in the handle extension using a pliers or some other gripping device. Once inserted into the hole, the deformable enlarged portion prevents the escape of the ringlets during use, and the extension arm may be cut off. If another ringlet is to be installed, the enlarged portion is simply cut off from the installed ringlet and that ringlet discarded.

Figure 2A:
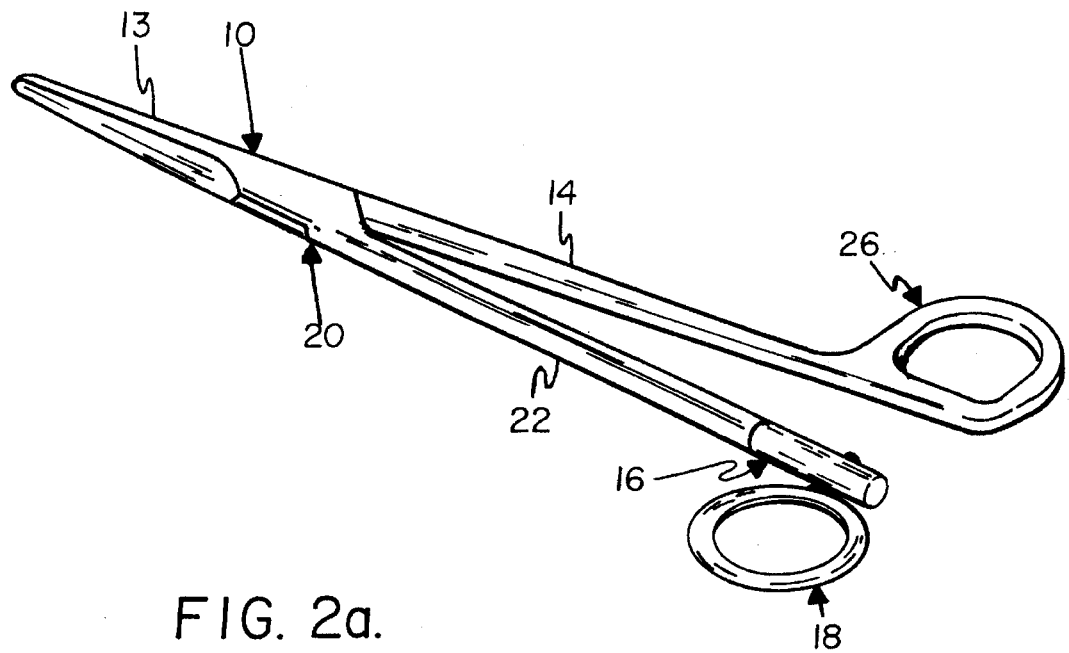
FIG. 2a is a schematic representation of a perspective view of the pivoted grasping instrument embodiment of the present invention shown in its closed configuration.
Figure 2B:
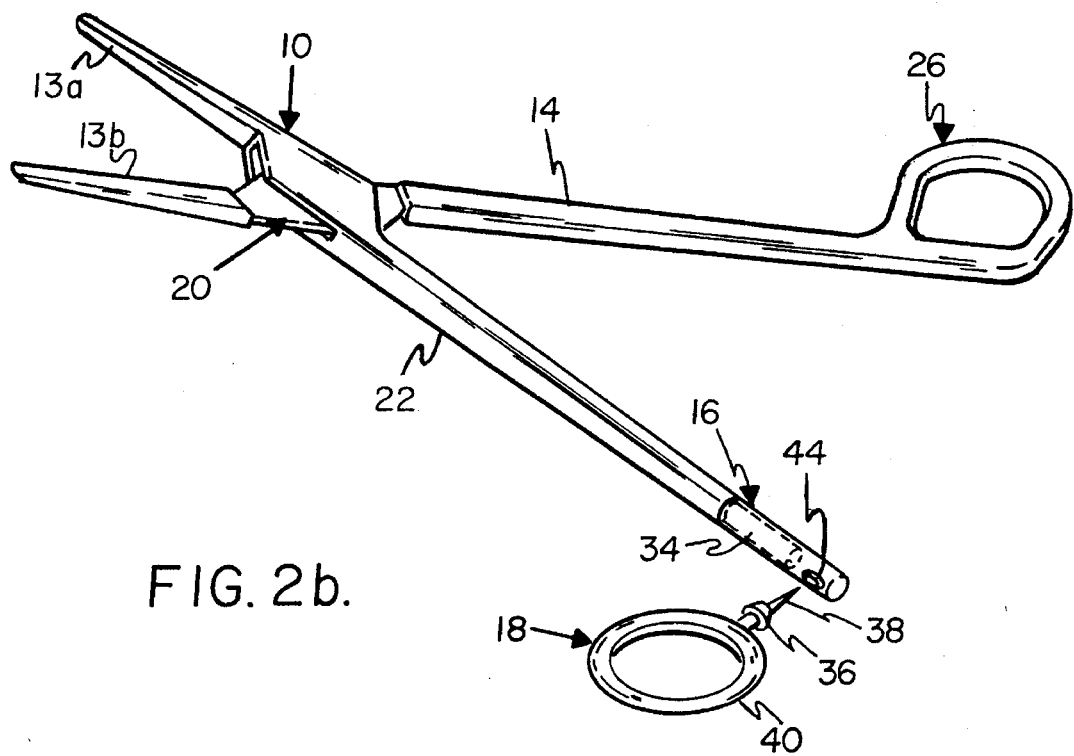
FIG. 2b is a schematic representation of an exploded view of the forceps illustrated in FIG. 2a hereof, showing, in particular, the forceps grasping surfaces, handles, and thumb ringlet.

FIG. 2a is a schematic representation of a perspective view of the pivoted grasping instrument embodiment of the present invention shown in its closed configuration. FIG. 2b is a schematic representation of an exploded view of the forceps illustrated in FIG. 2a hereof, showing, in particular, the forceps grasping surfaces, handles, and thumb ringlet. The principal differences between the scissors embodiment of the present invention shown in FIGS. 1a and 1b hereof, and the grasping instrument embodiment of the invention are that cutting surfaces 12a and 12b, shown FIG. 1b are replaced by grasping surfaces 13a and 13b, shown in FIG. 2b, that extension arm 16 in FIG. 2b illustrates the use of a simple hole 44 in which thumb ringlet 18 is inserted as opposed to the use of a tubular extension, shown in FIGS. 1a and 1b and explained more fully in FIG. 3 hereof, that screw 30 shown in FIGS. 1a and 1b is replaced by internal fastening means in FIGS. 2a and 2b, and that bumper 28 of the scissors embodiment does not appear in the forceps embodiment. Otherwise, the callouts refer to similar structure in both figures.

Figure 3:
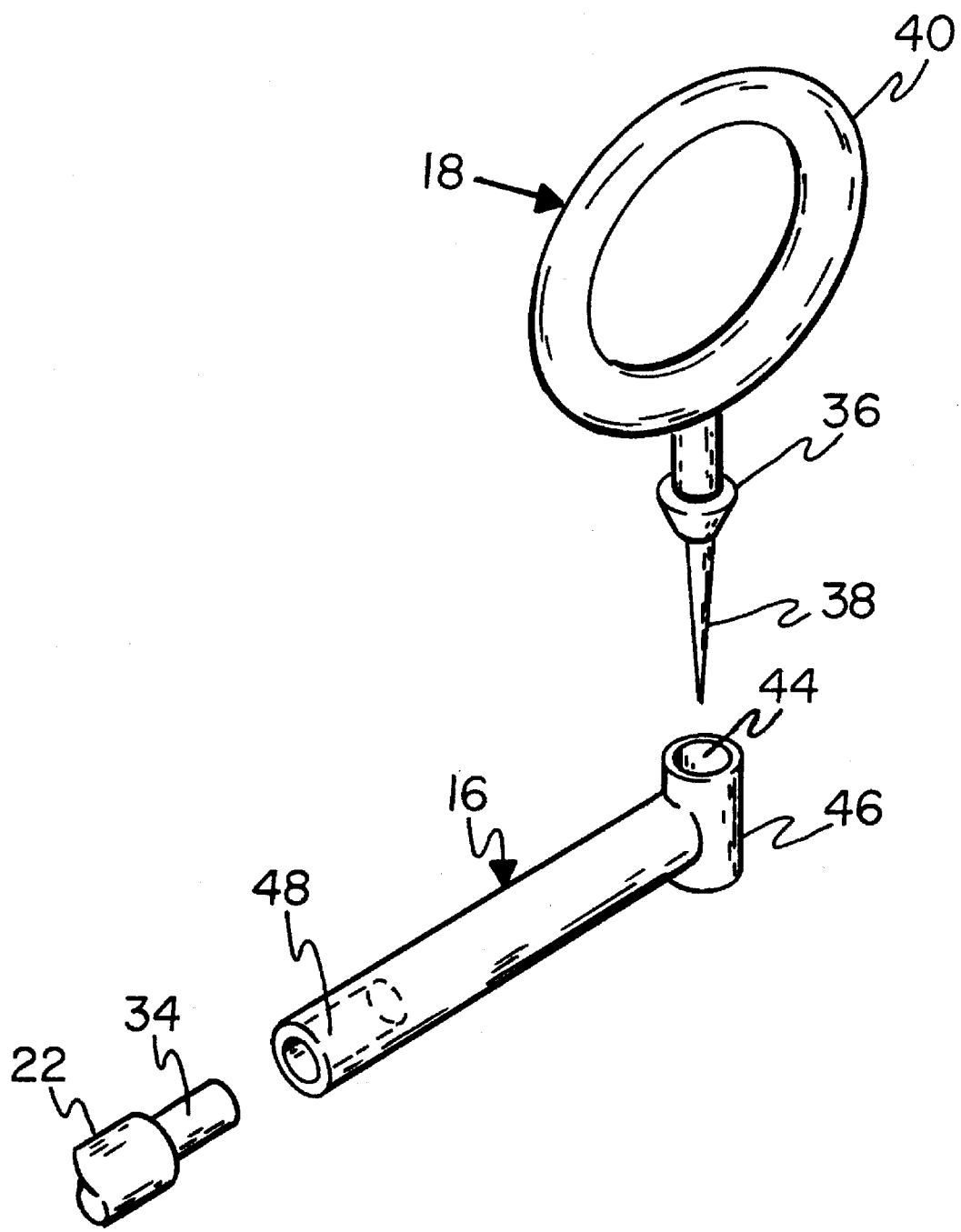
FIG. 3 is a schematic representation of an exploded view of the interrelationship among the handle extension means and the thumb ringlet of the present invention.

FIG.3 is a schematic representation of an exploded view of the thumb ringlet 18 of the present invention, and its interrelationship with handle extension means 16 and handle 22. handle extension 16 includes a tubular section 46 located at the terminus thereof having its axis disposed in a substantially perpendicular manner to the axis of the handle extension and adapted to receive ringlet 18. Handle extension 16 has a hole 48 bored along the axis thereof in order to enable it to receive the reduced diameter terminus 34 of scissors handle 22 to which it is rigidly attached. Handle extensions are preferably fabricated from plastic materials in order to reduce the cost and weight of the resulting pivoted instrument.

The foregoing description of several preferred embodiments of the invention has been presented for purposes of illustration and description, It is not intended to be exhaustive or to limit the invention to the precise form disclosed, and obviously many modifications and variations are possible in light of the above teaching. The embodiment s were chosen and described in order to best explain the principles of the invention and its practical application to thereby enable others skilled in the art to best utilize the invent ion in various embodiments and with various modifications as are suited to the particular use contemplated. It is intended that the scope of the invention be defined by the claims appended here to.

What we claim is:

1. A pair of scissors having an interchangeable thumb ringlet, comprising in combination:

a. a first shank member having a handle portion and a cutting portion approximately separated by a first pivot location;

b. elongated handle extension means rigidly attached to the handle portion of said first shank member substantially near to the terminus thereof away from the first pivot location, said handle extension means having a tubular portion located at the end thereof opposite the position of attachment thereof to said first shank member and disposed substantially perpendicular to the long dimension thereof;

c. flexible thumb ring means having a ring-shaped portion and a generally cylindrical arm attached radially thereto, the arm having an enlarged deformable terminus and an arm extension located on said cylindrical arm thereof on the opposite side of said enlarged deformable terminus thereof from said ring-shaped portion, said arm extension being adapted for insertion into the tubular portion of said handle extension means; and d. a second shank member having a handle portion, and a cutting portion approximately separated by a second pivot location, said second shank member being pivotably connected to said first shank member in the region of the first pivot location and the second pivot location in such a manner that the cutting portion of said first shank member and the cutting portion of said second shank member cooperate as opposing cutting portions of said pair of scissors; whereby the cylindrical arm of said thumb ring means, once inserted into the tubular portion of said handle extension means, forms said thumb ringlet, the enlarged terminus thereof and the ring-shaped portion preventing escape therefrom.

2. A pivoted grasping instrument having an interchangeable thumb ringlet, comprising in combination:

a. a first shank member having a handle portion and a grasping portion approximately separated by a first pivot location;

b. elongated handle extension means rigidly attached to the handle portion of said first shank member substantially near to the terminus thereof away from the first pivot location, said handle extension means having a tubular portion located at the end thereof opposite the position of attachment thereof to said first shank member and disposed substantially perpendicular to the long dimension thereof;

c. flexible thumb ring means having a ring-shaped portion and a generally cylindrical arm attached radially thereto, the arm having an enlarged deformable terminus and an arm extension located on said cylindrical arm thereof on the opposite side of said enlarged deformable terminus thereof from said ring-shaped portion, said arm extension being adapted for insertion into the tubular portion of said handle extension means; and d. a second shank member having a handle portion, and a grasping portion approximately separated by a second pivot location, said second shank member being pivotably connected to said first shank member in the region of the first pivot location and the second pivot location in such a manner that the grasping portion of said first shank member and the grasping portion of said second shank member cooperate as opposing grasping portions of said grasping instrument; whereby the cylindrical arm of said thumb ring means, once inserted into the tubular portion of said handle extension means, forms said thumb ringlet, the enlarged terminus thereof and the ring-shaped portion preventing escape therefrom.

3. A pair of scissors having an interchangeable thumb ringlet, comprising in combination:

a. a first shank member having a handle portion and a cutting portion approximately separated by a first pivot location, the handle portion thereof having a tubular portion located at the end thereof opposite the position of the first pivot location and disposed substantially perpendicular to the long dimension thereof;

b. flexible thumb ring means having a ring-shaped portion and a generally cylindrical arm attached radially thereto, the arm having an enlarged deformable terminus and an arm extension located on said cylindrical arm thereof on the opposite side of said enlarged deformable terminus thereof from said ring-shaped portion, said arm extension being adapted for insertion into the tubular portion of said first shank member; and c. a second shank member having a handle portion, and a cutting portion approximately separated by a second pivot location, said second shank member being pivotably connected to said first shank member in the region of the first pivot location and the second pivot location in such a manner that the cutting portion of said first shank member and the cutting portion of said second shank member cooperate as opposing cutting portions of said pair of scissors; whereby the cylindrical arm of said thumb ring means, once inserted into the tubular portion of said first shank member, forms said thumb ringlet, the enlarged terminus thereof and the ring-shaped portion preventing escape therefrom.

4. A pivoted grasping instrument having an interchangeable thumb ringlet, comprising in combination:

a. a first shank member having a handle portion and a grasping portion approximately separated by a first pivot location the handle portion thereof having a tubular portion located at the end thereof opposite the position of the first pivot location disposed substantially perpendicular to the long dimension thereof;

b. flexible thumb ring means having a ring-shaped portion and a generally cylindrical arm attached radially thereto, the arm having an enlarged deformable terminus and an arm extension located on said cylindrical arm thereof on the opposite side of said enlarged deformable terminus thereof from said ring-shaped portion, said arm extension being adapted for insertion into the tubular portion of said first shank member; and c. a second shank member having a handle portion, and a grasping portion approximately separated by a second pivot location, said second shank member being pivotably connected to said first shank member in the region of the first pivot location and the second pivot location in such a manner that the grasping portion of said first shank member and the grasping portion of said second shank member cooperate as opposing grasping portions of said grasping instrument; whereby the cylindrical arm of said thumb ring means, once inserted into the tubular portion of said first shank member, forms said thumb ringlet, the enlarged terminus thereof and the ring-shaped portion preventing escape therefrom.

5. A pair of scissors having an interchangeable thumb ringlet comprising in combination:

a. a first shank member having a handle portion and a cutting portion approximately separated by a first pivot location, the handle portion thereof having a hole therein located in the vicinity of the end thereof opposite the position of the first pivot location and disposed substantially perpendicular to the long dimension thereof;

b. flexible thumb ring means having a ring-shaped portion and a generally cylindrical arm attached radially thereto, the arm having an enlarged deformable terminus and an arm extension located on said cylindrical arm thereof on the opposite side of said enlarged deformable terminus thereof from said ring-shaped portion, said arm extension being adapted for insertion into the hole in said first shank member; and c. a second shank member having a handle portion, and a cutting portion approximately separated by a second pivot location, said second shank member being pivotably connected to said first shank member in the region of the first pivot location and the second pivot location in such a manner that the cutting portion of said first shank member and the cutting portion of said second shank member cooperate as opposing cutting portions of said pair of scissors; whereby the cylindrical arm of said thumb ring means, once inserted into the hole in said first shank member, forms said thumb ringlet, the enlarged terminus thereof and the ring-shaped portion preventing escape therefrom.

6. A pivoted grasping instrument having an interchangeable thumb ringlet, comprising in combination:

a. a first shank member having a handle portion and a cutting portion approximately separated by a first pivot location, the handle portion thereof having a hole therein located in the vicinity of the end thereof opposite the position of the first pivot location and disposed substantially perpendicular to the long dimension thereof;

b. flexible thumb ring means having a ring-shaped portion and a generally cylindrical arm attached radially thereto, the arm having an enlarged deformable terminus and an arm extension located on said cylindrical arm thereof on the opposite side of said enlarged deformable terminus thereof from said ring-shaped portion, said arm extension being adapted for insertion into the hole in said first shank member; and c. a second shank member having a handle portion, and a cutting portion approximately separated by a second pivot location, said second shank member being pivotably connected to said first shank member in the region of the first pivot location and the second pivot location in such a manner that the grasping portion of said first shank member and the grasping portion of said second shank member cooperate as opposing grasping portions of said grasping instrument; whereby the cylindrical arm of said thumb ring means, once inserted into the hole in said first shank member, forms said thumb ringlet, the enlarged terminus thereof and the ring-shaped portion preventing escape therefrom.

* * * * *